(12) United States Patent
Miller et al.

(10) Patent No.: US 10,058,877 B2
(45) Date of Patent: Aug. 28, 2018

(54) CENTRIFUGE LOADING/UNLOADING APPARATUS, SYSTEMS, AND METHODS

(71) Applicant: Siemens Healthcare Diagnostics Inc., Tarrytown, NY (US)

(72) Inventors: Kerry Miller, Elkton, MD (US); Steven Sparks, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 365 days.

(21) Appl. No.: 14/773,248

(22) PCT Filed: Mar. 7, 2014

(86) PCT No.: PCT/US2014/021533
§ 371 (c)(1),
(2) Date: Sep. 4, 2015

(87) PCT Pub. No.: WO2014/138524
PCT Pub. Date: Sep. 12, 2014

(65) Prior Publication Data
US 2016/0023220 A1 Jan. 28, 2016

Related U.S. Application Data

(60) Provisional application No. 61/775,148, filed on Mar. 8, 2013.

(51) Int. Cl.
*B04B 5/10* (2006.01)
*B04B 11/04* (2006.01)
(Continued)

(52) U.S. Cl.
CPC ............ *B04B 11/04* (2013.01); *B04B 5/0414* (2013.01); *B04B 5/10* (2013.01); *B04B 13/00* (2013.01);
(Continued)

(58) Field of Classification Search
CPC ......... B04B 5/10; B04B 13/00; B04B 5/0407; B04B 9/00; B04B 5/0421; B04B 5/0414;
(Continued)

(56) References Cited

U.S. PATENT DOCUMENTS 3,151,073 A * 9/1964 Anthon ................ B04B 5/04
198/803.9
3,644,095 A * 2/1972 Netheler ............ G01N 35/0092
141/130

(Continued)

FOREIGN PATENT DOCUMENTS

JP 2004230328 A * 8/2004 ............ B04B 5/0421
JP 2004230329 A * 8/2004 ............ B04B 5/0421
(Continued)

OTHER PUBLICATIONS

PCT International Search Report and Written Opinion dated Aug. 19, 2014 (9 Pages).

*Primary Examiner* — Charles E Cooley (57) ABSTRACT

A loading and unloading system loads/unloads a sample processor (e.g., a centrifuge). The system includes a staging area containing inserts, at least one being a common insert, the sample processor having locations receiving inserts containing unprocessed sample containers, one or more robots operable to move unprocessed and processed sample containers to and from the common insert as well as move the inserts between the staging area and the sample processor, and a controller commanding the one or more robots to carry out a sample container movement sequence to load and unload unprocessed and processed sample containers to and from the common insert at the staging area, wherein the common bucket insert contains both processed and unprocessed sample containers at a same time. Methods of operating the system are provided.

17 Claims, 4 Drawing Sheets

(51) Int. Cl.
  *B04B 13/00* (2006.01)
  *B04B 5/04* (2006.01)
  *B25J 11/00* (2006.01)
  *G01N 35/00* (2006.01)

(52) U.S. Cl.
  CPC ......... *B25J 11/00* (2013.01); *B04B 2011/046* (2013.01); *G01N 2035/00495* (2013.01)

(58) Field of Classification Search
  CPC ....... B04B 2011/046; B04B 9/10; B04B 5/00; B04B 11/04; G01N 35/04; G01N 35/00; G01N 2035/0465; G01N 2035/00495; G01N 2035/0406; G01N 35/02; G01N 35/0092; G01N 2035/0094
  See application file for complete search history.

(56) References Cited

U.S. PATENT DOCUMENTS

| | | | | |
|---|---|---|---|---|
| 5,623,415 A * | 4/1997 | O'Bryan | G01N 35/021 | 198/617 |
| 5,674,322 A * | 10/1997 | Kunz | B04B 5/10 | 127/53 |
| 5,721,676 A * | 2/1998 | Bolden | A61M 1/387 | 422/72 |
| 5,740,185 A * | 4/1998 | Bosse | G11B 20/1833 | 356/39 |
| 5,814,276 A * | 9/1998 | Riggs | G01N 35/04 | 422/549 |
| 5,865,718 A * | 2/1999 | Chan | B04B 13/00 | 494/10 |
| 6,461,287 B1 * | 10/2002 | Glater | B01D 3/08 | 159/DIG. 11 |
| 7,195,737 B2 * | 3/2007 | Itoh | B04B 5/0421 | 422/65 |
| 8,617,041 B2 * | 12/2013 | Haechler | B04B 13/00 | 422/72 |
| 8,795,144 B2 * | 8/2014 | Pedrazzini | B04B 5/0421 | 494/20 |
| 9,889,453 B2 * | 2/2018 | Itoh | B04B 5/10 | |
| 2004/0022682 A1 * | 2/2004 | Itoh | G01N 35/04 | 422/64 |
| 2004/0089737 A1 * | 5/2004 | Itoh | B04B 5/0421 | 239/264 |
| 2004/0102920 A1 * | 5/2004 | Itoh | B04B 5/0414 | 702/173 |
| 2004/0184958 A1 * | 9/2004 | Itoh | B04B 5/0421 | 422/72 |
| 2004/0184959 A1 * | 9/2004 | Itoh | B04B 5/0421 | 422/72 |
| 2007/0020764 A1 * | 1/2007 | Miller | G01N 35/0092 | 436/45 |
| 2007/0059209 A1 * | 3/2007 | Pang | G01N 35/0095 | 422/72 |
| 2009/0003981 A1 * | 1/2009 | Miller | B65G 1/04 | 414/267 |
| 2009/0047179 A1 * | 2/2009 | Ping | G01N 35/0095 | 422/72 |
| 2009/0275458 A1 * | 11/2009 | Dee | G01N 35/0095 | 494/10 |
| 2009/0318276 A1 * | 12/2009 | Miller | B04B 13/00 | 494/20 |
| 2011/0045958 A1 * | 2/2011 | Pedrazzini | B04B 5/0421 | 494/8 |
| 2011/0245061 A1 * | 10/2011 | Haechler | B04B 13/00 | 494/8 |
| 2012/0129673 A1 * | 5/2012 | Fukugaki | G01N 35/00029 | 494/1 |
| 2013/0307381 A1 * | 11/2013 | Itoh | G01N 35/04 | 312/97 |
| 2015/0111299 A1 * | 4/2015 | Watabe | G01N 35/0095 | 436/45 |
| 2015/0141232 A1 * | 5/2015 | Verweij | B04B 5/10 | 494/16 |
| 2015/0360239 A1 * | 12/2015 | Yano | B04B 13/00 | 494/10 |
| 2016/0016183 A1 * | 1/2016 | Miller | B04B 5/0414 | 494/1 |
| 2016/0023220 A1 * | 1/2016 | Miller | B04B 5/0414 | 494/16 |
| 2017/0021367 A1 * | 1/2017 | Itoh | B04B 5/0407 | |
| 2017/0219616 A1 * | 8/2017 | Pedrazzini | G01N 35/00009 | |

FOREIGN PATENT DOCUMENTS

| | | | | |
|---|---|---|---|---|
| JP | 2011056397 A * | 3/2011 | ............ | B04B 5/10 |
| JP | 2011189324 A * | 9/2011 | ............ | B04B 13/00 |

* cited by examiner

CENTRIFUGE LOADING/UNLOADING APPARATUS, SYSTEMS, AND METHODS

CROSS-REFERENCE TO RELATED APPLICATIONS

This application claims priority to U.S. Provisional Application Ser. No. 61/775,148 filed Mar. 8, 2013, which is incorporated herein by reference in its entirety.

FIELD

The present invention relates generally to methods of automated loading and unloading a centrifuge.

BACKGROUND

In medical testing and processing, the use of robotics may minimize exposure to, or contact with, bodily fluid samples (otherwise referred to as "specimens") and/or may increase productivity. For example, in some existing automated testing and processing systems (e.g., centrifuges), sample containers (such as blood collection tubes or the like) may be transported from an automated conveyor system by a transfer robot, and placed in an incoming bucket insert located within an incoming staging area. Bucket inserts are multi-receptacle containers that have numerous receptacles (e.g., 20 receptacles) adapted to receive sample containers. An incoming bucket insert, once filled, is then transported from the input staging area to a bucket of a centrifuge. This process is continued until the buckets of the centrifuge are appropriately filled, as desired. The samples are then centrifuged by spinning at high RPM to separate the whole blood and serum components (e.g., blood components). The time needed for full centrifuging may be between about 8-12 minutes.

Once centrifugation is complete, the bucket inserts are moved by a robot to an outgoing staging area, and a transfer robot then may proceed to empty the outgoing bucket insert and place the samples back onto the automated conveyor system. Once emptied, the outgoing bucket insert may be moved from the outgoing staging area to an incoming staging area, become an incoming bucket insert and again be filled with incoming sample containers to be centrifuged. This process allows near constant flow of sample containers into and out of the centrifuge. Typically, the incoming staging area includes a scale for obtaining the weights of the incoming bucket inserts and sample containers provided therein.

Although this loading/unloading system and method provides suitable efficiencies, more efficient systems and methods are sought to further reduce both processing time and cost. Accordingly, systems and methods that may improve speed of moving sample containers to and from testing and processing systems (e.g., centrifuges) are desired.

SUMMARY

According to a first aspect, an improved method of loading and unloading a centrifuge is provided. The method includes providing a staging area having multiple bucket inserts, providing a centrifuge having multiple buckets adapted to receive bucket inserts containing sample containers, and loading and unloading sample containers to and from a common bucket insert of the multiple bucket inserts at the staging area, wherein the common bucket insert contains both processed sample containers and unprocessed sample containers at a same time.

In an apparatus aspect, a centrifuge loading and unloading system is provided. The centrifuge loading and unloading system includes a staging area containing multiple bucket inserts at least one being a common bucket insert; a centrifuge having buckets adapted to receive bucket inserts containing unprocessed sample containers, one or more robots operable to move unprocessed sample containers to the common bucket insert and remove processed sample containers from the common bucket insert and move the bucket inserts between the staging area and the buckets of the centrifuge, and a controller operable to command the one or more robots to carry out a sample container movement sequence to move unprocessed sample containers to the common bucket insert at the staging area and remove processed sample containers from the common bucket insert, wherein the common bucket insert contains both processed sample containers and unprocessed sample containers at a same time.

In another apparatus aspect, a loading and unloading apparatus is provided. The apparatus includes a source of unprocessed sample containers, a staging area containing multiple inserts adapted to receive sample containers, at least one of which is a common sample insert, a sample processor having multiple locations adapted to receive inserts, a robot adapted to move the inserts between the staging area and the multiple locations, and a controller operational to cause the robot to execute a sample container movement sequence to move sample containers to and from one or more of the inserts at the staging area, wherein one or more of the inserts contain both processed sample containers and unprocessed sample containers at a same time.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

DETAILED DESCRIPTION

In current centrifuging systems, it is desired to load and unload centrifuge bucket inserts to and from centrifuge buckets concurrently to the operation of the centrifuge to efficiently utilize this resource.

Figure 1:
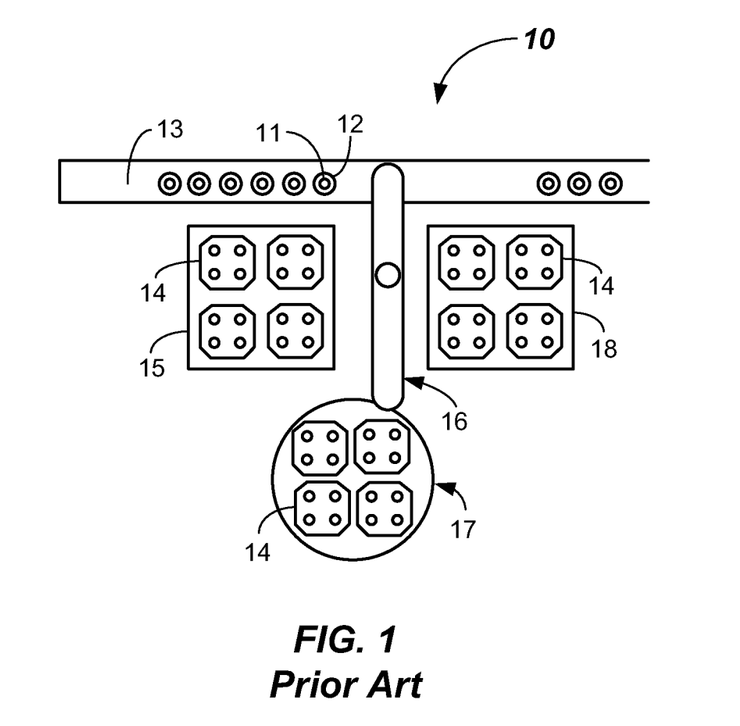
FIG. 1 illustrates an example centrifuge loading and unloading system according to the prior art.

Current centrifuge loading and unloading systems 10, as shown in FIG. 1, utilize an approach whereby the input processing and output processing of sample containers is physically segregated. In particular, centrifuge loading and unloading station 10, like those disclosed in U.S. Pat. No. 6,060,022 and U.S. Pat. No. 6,589,789, are adapted to remove a sample container 11 carried by a sample container carrier 12 from track 13 and to place individual sample containers 11 in a weight-balanced pattern into open receptacles (not shown for purposes of clarity) in a centrifuge bucket insert 14 disposed temporarily on a first bucket weighing and loading platform 15 (the input staging area).

Centrifuge loading and unloading station 10 is provided with of bucket transfer device 16 adapted to remove a weight-balanced centrifuge bucket insert 14 from first loading platform 15 and to place the weight-balanced centrifuge bucket insect 14 into centrifuge 17 for centrifuging. In order to avoid an unbalanced centrifuging condition, additional weight-balanced centrifuge bucket inserts 14 are loaded on the first loading platform 15 placed into centrifuge 17 so as to maintain an overall balanced load within centrifuge 17. Typically, centrifuge bucket inserts 14 are placed into centrifuge 17 in opposing pairs.

After centrifuging is complete, centrifuge loading and unloading station 10 utilizes bucket transfer device 16 to remove a centrifuge bucket insert 14 from centrifuge 17 one after another and to place each centrifuge, bucket insert 14 on a first bucket unloading platform 18 (an output staging area). For purposes of simplicity, only four sample containers 11 are illustrated in each centrifuge bucket insert 14, while in practice a larger number on the order of 10-20 sample containers 11 are typically placed into each centrifuge bucket insert 14.

Finally, bucket transfer device 16 is adapted to remove centrifuged sample containers 11 from bucket insert 14 disposed on first bucket unloading platform 18 and to replace the now-centrifuged sample containers 11 into carriers 12 on track 13 for subsequent pre-analytical processing and/or for analysis. After all centrifuged sample containers 11 have been removed from a centrifuge bucket insert 14, the empty centrifuge bucket insert 14 is moved from unloading platform 18 and onto the loading platform 15. This loading and unloading process is continued until all of the sample containers 11 in sample carriers 12 requiring some form of separation have been centrifuged and replaced onto conveyor track 13. This prior art process makes sample container management relatively easy. However, it also may introduce numerous inefficiencies. In particular, using this two-sided centrifugation with separated loading and unloading stations is wasteful since there are many bucket inserts that need to be moved around. Furthermore, it takes time to move the robotic arm from side to side when loading and unloading bucket inserts 14 into and out of the centrifuge 17 and sample containers 11 into and out of the bucket inserts 14. Any time the centrifuge is not processing sample containers 11 is a lost opportunity cost.

In view of the foregoing problems, embodiments of the present invention in one aspect provide methods, systems, and apparatus adapted and operational to load and unload bucket inserts from a centrifuge. The system and method may reduce the overall time it takes to load and unload a batch of sample containers. In particular, time is saved by minimizing a number of robot motions (moves) as well as the distance traveled by the robot (travel path). Thus, in a first aspect, a method of loading and unloading a centrifuge is provided that includes loading and unloading sample containers to and from a common bucket insert (e.g., at a staging area), wherein the common bucket insert contains both centrifuged samples and un-centrifuged samples at a same time. This method may also reduce the number of bucket inserts utilized, thereby reducing costs. Sample status, whether processed (e.g., separated) or unprocessed (e.g., not separated), specimen identity, sample container weight, and sample container location is constantly managed.

These and other aspects and features of embodiments of the invention will be described with reference to FIGS. 2-4 herein.

Figure 2:
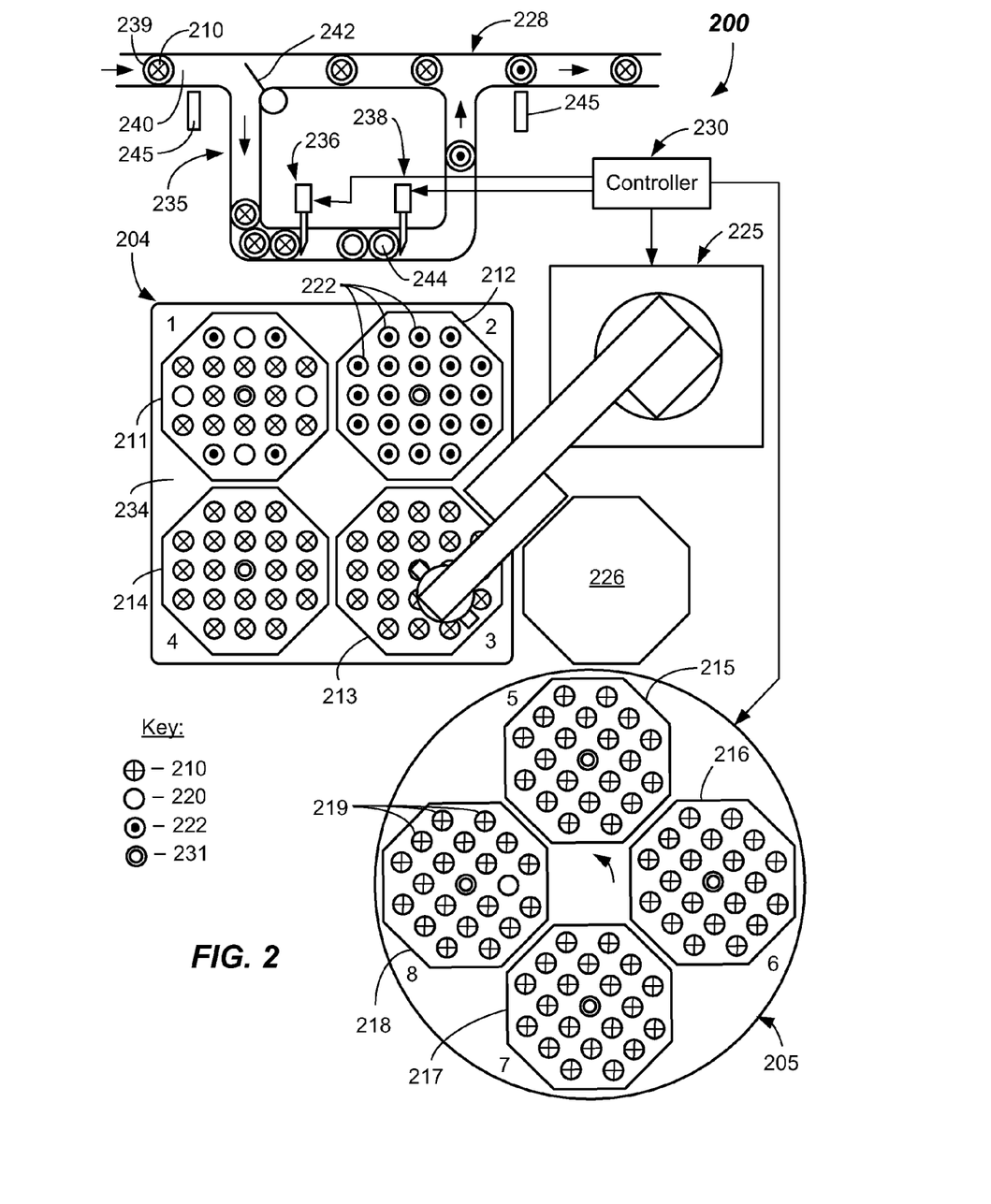
FIG. 2 illustrates a graphical diagram of a loading and unloading system according to embodiments.

In accordance with a first embodiment of the invention, as best shown in FIG. 2, a centrifuge loading and unloading system 200 is described. The centrifuge loading and unloading system 200 is useful for reducing the time to load and unload a centrifuge, for example. In particular, the described embodiment includes a staging area 204 containing multiple locations labeled 1, 2, 3, 4 supporting multiple inserts, such as bucket inserts 211-214. At least one of the bucket inserts 211-214 being a common bucket insert (e.g., 211) will be described later herein. The staging area 204 may be a platform adapted to receive the bucket inserts 211-214 and include a weight scale (not shown), which may be positioned underneath the platform to provide a weight of the bucket inserts 211-214 and their contents.

The system 200 further includes a processing system such as a centrifuge 205 having multiple locations such as buckets 5, 6, 7, 8 that are adapted to receive inserts, such as bucket inserts 215-218. The buckets 5-8 may be of any shape and configuration to accept and position the bucket inserts 215-218. Bucket inserts 215-218 received into the buckets 5-8 may contain unprocessed sample containers 210, as shown. Unprocessed sample containers 210 are sample containers, such as blood collection tubes and the like, that contain a specimen (e.g., blood) to be processed (e.g., centrifuged). Unprocessed sample containers 210 are labeled with a cross herein. Prior to processing (e.g., centrifuging), all of the receptacles 219 (a few labeled) in the bucket inserts 215-218 may be full. In other embodiments, at least some receptacles 219 may be empty. Empty receptacles 220 are designated as O's herein.

After processing (e.g., centrifuging) a batch has taken place, such as by spinning the bucket inserts 211-214 containing unprocessed sample containers 210 in the centrifuge 205 at a sufficient speed (e.g., between about 3000 RPM and 4000 RPM) for a sufficient time (e.g., between about 8 min and about 12 min), for example, the sample containers now contain processed specimens (e.g., that have been separated into their constituent components of whole blood and serum portions, and possibly a separation layer) and are now designated as processed sample containers 222. Processed sample containers 222 are designated herein by having a dot therein. For example, location 2 at the staging area 204 is shown including a bucket insert 212 having processed sample containers 222 that have been removed from the centrifuge 205 in a previous batch.

The system 200 further includes one or more robots 225 positioned adjacent the staging area 204, the centrifuge 205, and a temporary storage location 226. The one or more robots 225 are operable to: 1) move unprocessed sample containers 210 to the common bucket insert 211 and remove processed sample containers 222 from the common bucket insert 211, and move the bucket inserts (e.g., 214, etc.) between the staging area 204 and the buckets 5-8 of the centrifuge 205. Thus, the robot 225 functions to load and unload the bucket inserts 211-218 and load and unload the unprocessed sample containers 210 and processed sample containers 222 to and from a conveyor system 228.

In addition, the system 200 includes a controller 230 operable to command and cause the one or more robots (e.g., robot 225) to carry out a sample container movement sequence to move unprocessed sample containers 210 to the common bucket insert (e.g., 211) at the staging area 204 and remove processed sample containers 222 from the common bucket insert (e.g., 211), wherein the common bucket insert (e.g., 211) contains both unprocessed sample containers 210 and processed sample containers 222 at a same time.

The robot 225 may be any suitable robot adapted to move the unprocessed sample containers 210 from the conveyor system 228 to the staging area 204, and processed sample containers 222 to the conveyor system 228 from the staging area 204. The same robot 225 may also move the bucket inserts 211-214 to the buckets 5-8 of the centrifuge 205, remove the bucket inserts 215-218 from the centrifuge 205, and also transport them to the temporary storage location 226. The bucket inserts 211-214 may be moved by grasping a central post 231 on each bucket insert 211-218. The central post 231 is designated herein as an unfilled circle within a circle.

The robot 225 may be a multi-arm robot, such as a selective compliance articulated robot arm (SCARA) robot, gantry robot, or the like. Other types of robots may be used. The robot 225 may include one or more shoulder, elbow, or wrist elements to accomplish three-dimensional motion thereof. The robot 225 may have an end effector or finger set adapted to grasp the processed and unprocessed sample containers 210, 222, and also the central post 231 on the bucket inserts 211-218. The means for moving the components of the robot 225 may include any suitable conventional motion-producing mechanism, such as one or more stepper motors, servo motors, pneumatic or hydraulic motors, electric motors, or the like. Furthermore, drive systems including chains, guides, pulleys and belt arrangements, gear or worm drives or other conventional drive components may be utilized to cause the motion of the components of the robot 225. The conveyor system 228 may be any suitable conveyor capable of moving the sample containers 210, 222 to and from the staging area 204. Conveyor system 228 may include a moving belt or track, for example. Other gates and reader systems may be used on the conveyor system 228 to track a location of the samples entering and exiting from the staging area 204.

Figure 3A:
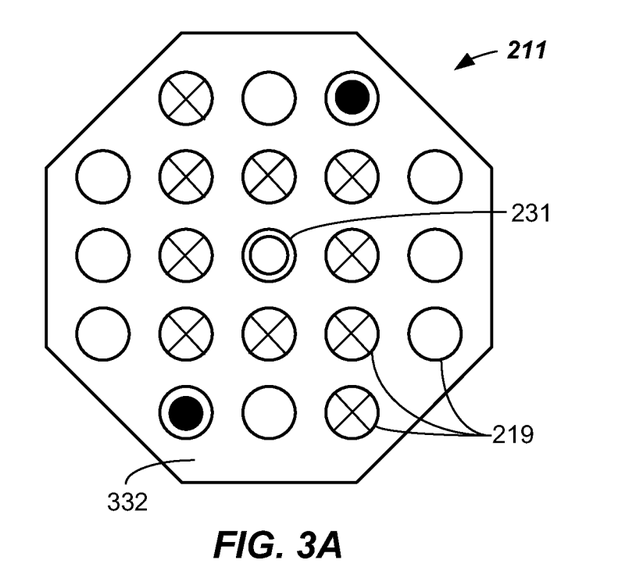
FIGS. 3A and 3B illustrate top and side plan views, respectively, of a common bucket insert containing sample containers according to embodiments.
Figure 3B:
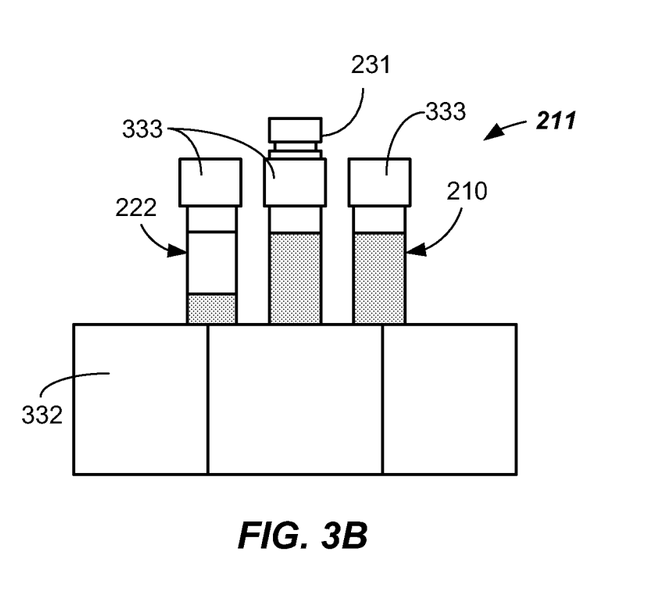
Figure 4:
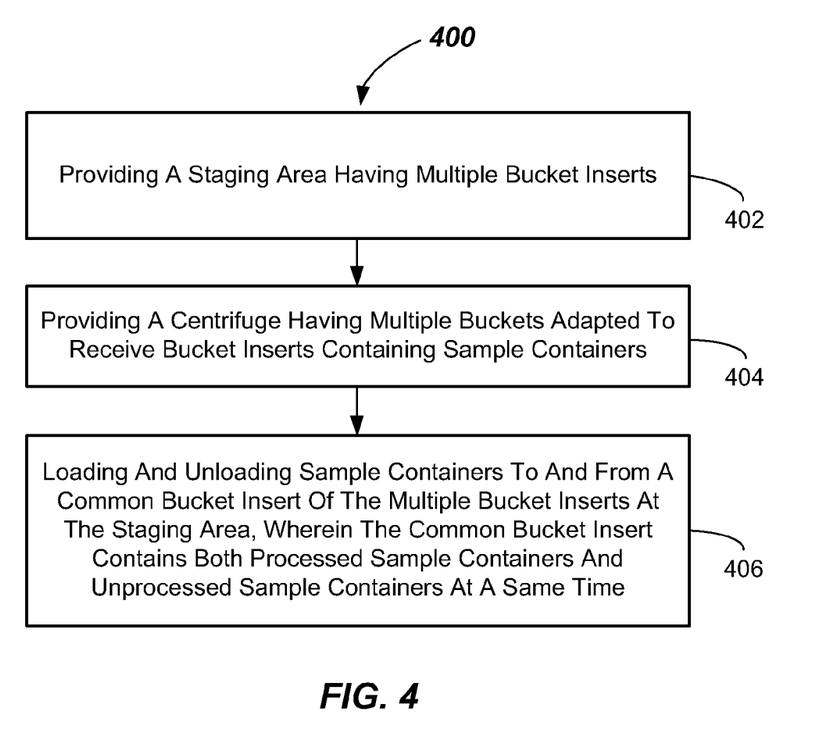
FIG. 4 illustrates a flowchart of a method according to embodiments.

A representative common bucket insert is shown in FIGS. 3A and 3B and includes a body 332 having the plurality of receptacles 219, and the central post 231 extending upward from the body 332 and configured to be grasped by the robot 225. The common bucket insert 211 may contain unprocessed sample containers 210 having blood therein, processed sample containers 222 having been centrifuged to separate the blood components, and may contain at least some empty receptacles 220. All of the sample containers 210, 222 may be capped with a conventional cap 333.

The system 200 depicted includes a centrifuge 205 adapted to separate various components of specimens provided therein. In particular, the centrifuge 205 may be a Hettich centrifuge available from Hettich Centrifuges of Beverly, Mass., which is adapted to receive bucket inserts 211-218 (sometimes referred to as "sample cassettes") into the buckets 5-8 which may be pivotally mounted to a yoke (not shown) of the centrifuge 205.

Again referring to FIG. 2, the staging area 204 may include a tray 234 which may be coupled to and supported by a weighing mechanism such as a weight scale (not shown) that is adapted to measure the weight of each of the bucket inserts 211-214, resting on the tray 234 and to determine the weight of each unprocessed sample container 210 as the unprocessed sample container 210 is added into a bucket insert 211-214. The controller 230 may record the weight, an identity of the bucket insert 211-214 receiving the sample container 210, and the receptacle location in the bucket insert 211-214 of each of the unprocessed sample containers 210. Each location may be given an indicia or name in tracking software. As the bucket inserts 211-218 progress through the system 200 and are, in sequence, transferred to the temporary storage area 226, from the staging area 204, to the centrifuge 205, and back to the staging area 204, the orientation of each of the bucket inserts 211-218 may be retained so that the exact location of the sample containers 210, 222 in the receptacles 219 is known at all times. As the processed sample containers 222 are removed, that information is used to update the software and database. Thus, for each of the bucket inserts 211-214 that are common bucket inserts the identity and type of sample container in each receptacle 219 is known and tracked. A location of empty receptacles 220 of the common bucket insert (and/or in other bucket inserts) may also be tracked.

The number of the common bucket inserts at the staging area 204 may be one, two, three, or four. The number of common bucket inserts may diminish as the bucket inserts are filled with unprocessed samples in preparation for loading the next batch. A common bucket insert is defined herein as a bucket insert that contains both unprocessed sample containers 210 and processed sample containers 222 at a same time. The common insert may also contain empty receptacles 220.

As a batch has completed processing at the centrifuge 205, the robot 225 may unload the bucket inserts 215-218 one by one. One sample container movement sequence that may be carried out by the robot 225 caused by commands from the controller 230 is shown in Table 1 below.

TABLE 1

Bucket Insert Movement Sequence

| Movement | Time (s) |
| --- | --- |
| 1 to Temp Storage Location | 9 |
| 5 to 1 | 9 |
| 2 to 5 | 9 |
| 6 to 2 | 9 |
| 3 to 6 | 9 |
| 7 to 3 | 8 |
| 4 to 7 | 10 |
| 8 to 4 | 9 |
| Temp Storage Location to 8 | 7 |

To start the loading and unloading process, one bucket insert that is ready for processing is placed at the temporary storage location 226. Following this, the bucket insert movement sequence may be followed whereby a processed bucket insert (e.g., bucket insert 215) is removed from the centrifuge 205 and placed into the staging area 204 and an unprocessed bucket insert (e.g., bucket insert 212) is placed in the bucket just vacated (e.g., bucket 5). At the end of a batch, or intermittently during the bucket insert movement sequence, loading and unloading from the one or more common bucket inserts (e.g., 211) may be accomplished. The goal is to provide one or more unprocessed bucket inserts (e.g., 213, 214) as soon as possible so that it may take the place of a processed bucket insert when a batch has completed centrifuging. Bucket inserts containing STAT specimens may be loaded first and also unloaded first from the centrifuge 205. Likewise, a processed sample container 222 containing a STAT specimen from the bucket insert first removed from the centrifuge 205 may be immediately loaded to the loading station 238 before loading processed sample containers containing non-STAT specimens and before loading a bucket insert having unprocessed sample containers 210 to the bucket vacated.

During the loading process, a balancing process may be enacted to ensure the various bucket inserts 215-218 at buckets 5-8 of the centrifuge 205 are appropriately weight balanced. Any suitable weight-balancing method may be used. For example, the various bucket inserts 211-214 at the staging area 204 may be loading to approximately balance the weight of each bucket insert 211-214 by monitoring the change in weight as sample containers 210, 222 are added and removed. Optionally, the bucket inserts may be loaded and unloaded in a pre-defined pattern and one or more empty receptacles 220 may be provided in each. These empty receptacles 220 may be filled with weights during weight balancing, and may have a shape to be received in one or more the empty receptacles 220, and used to suitable balance the centrifuge 205. Other loading and unloading schemes may be employed.

Furthermore, although the depicted examples are directed at a processing system that includes a centrifuge 205, it should be understood that the present invention system 200 may have utility for loading and unloading inserts containing sample containers from other types of automated processing systems as well as testing systems.

One loading and unloading apparatus and process that may be used with the system 200 includes providing a loading/unloading lane 235 on the conveyor system 228. The loading/unloading lane 235 may include an unloading station 236 and a loading station 238, which may be located downstream of the unloading station 236. The unloading station 236 provides a source of unprocessed sample containers 210. Unloading station 236 may receive carriers 239 containing unprocessed sample containers 210 that have been diverted from a main lane 240 by a diverter mechanism 242. Any suitable diverter mechanism 242 may be used that may either divert carriers 239 or leave the carriers 239 to continue along on the main lane 240, as desired. For example, in some instances, carriers 239 may be allowed to travel to another centrifuge or another processing location. The diverter 242 may have two positions; one for diverting, and one that allows the carrier 239 to continue on along the main lane 240.

During an unload/load sequence, a processed sample container 222 may be picked up from a bucket insert (e.g., 212 that has just been unloaded from a centrifuged batch by an end effector of the robot 225. The end effector may be an opposed set of gripper fingers, for example. The gripper fingers may be driven to open and close by a suitable end effector drive apparatus, such as a servo motor or the like. Any suitable mechanism for causing gripping action of the fingers may be used. The processed sample container 222 may be carried directly to the loading station 238 by the robot 225 and placed in an empty carrier 244 staged at the loading station 238. Once loaded, the carrier 244 may be released from station 238 by any suitable release mechanism and may move towards and reenter the main lane 240, where the processed sample container may travel to other stations along the track for further analysis or testing. One or more readers 245, such as a barcode reader or the like may be provided at suitable positions along the main lane 240, or even at the loading/unloading lane 235 to enable tracking of the location of the various sample containers 210, 222 entering and exiting the system 200 at the loading/unloading lane 235. This information may be sent to an automated laboratory system (LAS) computer for tracking a location and status of the sample containers 210, 222.

Once the robot 225 has delivered the processed sample container 222, the robot end effector may move directly to the unloading station 236 and may unload an unprocessed sample container 210 from a carrier 239 at the unloading station 236. This unprocessed sample container 210 may be inserted into the previously emptied empty receptacle 220, to fill the space and thus convert the bucket insert 212 into a common bucket insert containing both an unprocessed sample container 210 and processed sample containers 222 at a same time. In other embodiments, the unloaded unprocessed sample container 210 may be inserted into one of a plurality of available empty receptacles 220 in another common bucket insert (e.g., 211). This unload/load sample container movement sequence will continue until all of the processed sample containers 222 are unloaded to the loading station 238 and all the bucket inserts 211-214 are reloaded with unprocessed sample containers 210 from the unloading station 236 to a desired level of fullness. In some instances, the bucket inserts 211-214 will be full, and in others, some empty receptacles 220 will be provided. The bucket inserts (211-214) will again be moved to the centrifuge 205 by the robot 225 to be centrifuged in a next batch.

An embodiment of a method of loading and unloading a centrifuge will now be described with reference to FIG. 4. The method 400 includes, in 402, providing a staging area (e.g., staging area 204) having multiple bucket inserts (e.g., bucket inserts 211-214). More or less numbers of bucket inserts than those shown may be used. For example two or more may be used. For example, staging area 204 having two, three, four, five, or even six bucket inserts thereat may be used.

The method 400 also includes, in 404, providing a centrifuge (e.g., centrifuge 205) having multiple buckets (e.g., buckets 5-8) adapted to receive bucket inserts containing sample containers. The sample containers may be unprocessed sample containers 210 before centrifuging and processed sample containers 222 after. The number of buckets (e.g., 5-8) may be the same as or less than the number of bucket inserts (e.g., 211-214) at the staging area 204. However, in one or more embodiments, the number of buckets is equal to the number of bucket inserts at the storage area. For example, the system 200 may include four bucket inserts (e.g., bucket inserts (211-214) at the staging area 204, and four bucket inserts (e.g., bucket inserts 215-218) on the centrifuge 205. Thus, in one embodiment, eight or less bucket inserts are included in the system 200.

Additionally, the method 400 includes, in 406, loading and unloading sample containers (e.g., unprocessed sample containers 210 and processed sample containers 222) to and from a common bucket insert (e.g., bucket insert 211) of the multiple bucket inserts at the staging area. In accordance with embodiments of the invention, the common bucket insert (e.g., bucket insert 211) contains both processed sample containers 222 and unprocessed sample containers 210 at a same time. One or more of the bucket inserts 211-214 may be a common bucket insert.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed but, to the contrary, the intention is to cover all modifications, equivalents, and alternatives falling within the scope of the invention.

What is claimed is:

1. A method of loading and unloading a centrifuge, comprising:
providing a staging area having multiple bucket inserts;
providing a centrifuge having multiple buckets adapted to receive bucket inserts containing sample containers; and
loading and unloading sample containers to and from a common bucket insert of the multiple bucket inserts at the staging area, wherein the common bucket insert contains both processed sample containers and unprocessed sample containers at a same time.

2. The method of claim 1, further comprising providing at least some empty receptacles in the common bucket insert.

3. The method of claim 1, further comprising loading unprocessed sample containers to the common bucket insert from a conveyor system.

4. The method of claim 3, further comprising unloading processed sample containers from the common bucket insert to the conveyor system.

5. The method of claim 1, further comprising:
providing a temporary storage location; and
loading a bucket insert containing unprocessed sample containers to the temporary storage location.

6. The method of claim 1, further comprising:
unloading a STAT sample container from the common bucket insert first before non-STAT sample containers.

7. The method of claim 1, further comprising:
loading an unprocessed sample container into a receptacle of the common bucket insert vacated by a processed sample container.

8. The method of claim 1, further comprising:
tracking a location of processed sample containers and unprocessed sample containers contained in the common bucket insert.

9. The method of claim 1, further comprising:
tracking a location of empty receptacles of the common bucket insert.

10. A centrifuge loading and unloading system, comprising:
a staging area containing multiple bucket inserts, at least one being a common bucket insert;
a centrifuge having buckets adapted to receive bucket inserts containing unprocessed sample containers;
one or more robots operable to
move unprocessed sample containers to the common bucket insert and remove processed sample containers from the common bucket insert, and
move the bucket inserts between the staging area and the buckets of the centrifuge; and
a controller operable to command the one or more robots to carry out a sample container movement sequence to move unprocessed sample containers to the common bucket insert at the staging area and remove processed sample containers from the common bucket insert, wherein the common bucket insert contains both processed sample containers and unprocessed sample containers at a same time.

11. The centrifuge loading and unloading system of claim 10, further comprising:
a moving conveyor adapted to carry unprocessed sample containers to a loading station adjacent the staging area and processed sample containers away from an unloading station adjacent the staging area.

12. The centrifuge loading and unloading system of claim 10, further comprising eight or less bucket inserts in the system.

13. The centrifuge loading and unloading system of claim 10, further comprising a temporary storage location.

14. The centrifuge loading and unloading system of claim 10, further comprising:
a single robot operational to load unprocessed sample containers to the common bucket insert, and unload processed sample containers from the common bucket insert.

15. The centrifuge loading and unloading system of claim 10, wherein one or more of the common bucket inserts contain processed samples, unprocessed samples, and empty receptacles at a same time.

16. A loading and unloading apparatus, comprising:
a source of unprocessed sample containers;
a staging area containing multiple inserts adapted to receive sample containers, at least one of which is a common sample insert;
a sample processor having multiple locations adapted to receive inserts;
a robot adapted to move the inserts between the staging area and the multiple locations; and
a controller operational to cause the robot to execute a sample container movement sequence to move sample containers to and from one or more of the inserts at the staging area, wherein one or more of the inserts contain both processed sample containers and unprocessed sample containers at a same time.

17. The loading and unloading apparatus of claim 16, wherein one or more of the inserts contain processed sample containers, unprocessed sample containers, and empty receptacles at a same time.

* * * * *